United States Patent
Hede et al.

(10) Patent No.: US 10,711,262 B2
(45) Date of Patent: Jul. 14, 2020

(54) STORAGE-STABLE ENZYME GRANULES

(75) Inventors: Peter Dybdahl Hede, Copenhagen (DK); Ole Simonsen, Soeborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/232,076

(22) PCT Filed: Jul. 5, 2012

(86) PCT No.: PCT/EP2012/063131
§ 371 (c)(1),
(2), (4) Date: May 30, 2014

(87) PCT Pub. No.: WO2013/007594
PCT Pub. Date: Jan. 17, 2013

(65) Prior Publication Data
US 2014/0256610 A1    Sep. 11, 2014

Related U.S. Application Data

(60) Provisional application No. 61/506,839, filed on Jul. 12, 2011.

(30) Foreign Application Priority Data

Jul. 12, 2011 (EP) .................................... 11173592

(51) Int. Cl.
| | | |
|---|---|---|
| *C12N 11/14* | (2006.01) | |
| *C12N 9/98* | (2006.01) | |
| *C11D 3/386* | (2006.01) | |
| *C11D 3/37* | (2006.01) | |
| *C11D 17/00* | (2006.01) | |
| *C12N 9/20* | (2006.01) | |
| *C12N 9/42* | (2006.01) | |

(52) U.S. Cl.
CPC ............. *C12N 11/14* (2013.01); *C11D 3/3723* (2013.01); *C11D 3/38672* (2013.01); *C11D 17/0039* (2013.01); *C12N 9/20* (2013.01); *C12N 9/2437* (2013.01); *C12N 9/98* (2013.01)

(58) Field of Classification Search
CPC ........ B01D 61/24; B01D 63/00; C12N 11/06; C12N 9/20; C12N 9/98; C12N 9/2437; C12N 11/14; C11D 3/3723; C11D 3/38672; C11D 3/0036; C11D 17/0039
USPC ............................. 210/198.1, 632; 435/180
See application file for complete search history.

(56) References Cited

U.S. PATENT DOCUMENTS

| | | | | |
|---|---|---|---|---|
| 4,102,746 | A | * | 7/1978 | Goldberg ............... C12N 11/08 435/125 |
| 4,106,991 | A | * | 8/1978 | Markussen ........ C11D 3/38672 435/187 |
| 5,827,709 | A | * | 10/1998 | Barendse ....... C12Y 302/01004 435/188 |
| 5,972,669 | A | * | 10/1999 | Harz ........................ C12N 9/16 435/188 |
| 6,328,988 | B1 | * | 12/2001 | Uhrich ................. A61K 9/0014 424/422 |
| 6,376,445 | B1 | * | 4/2002 | Bettiol ................. C11D 3/0036 510/226 |
| 6,656,898 | B1 | * | 12/2003 | Foley et al. ................... 510/393 |
| 6,872,297 | B2 | | 3/2005 | Mansouri et al. |
| 7,115,173 | B2 | * | 10/2006 | Caswell et al. ................. 134/42 |
| 7,642,077 | B2 | * | 1/2010 | Bond ........................ C12N 9/54 435/176 |
| 2010/0078381 | A1 | | 4/2010 | Merchant |
| 2012/0164236 | A1 | * | 6/2012 | Iwasa ..................... A01N 59/16 424/616 |

FOREIGN PATENT DOCUMENTS

| | | |
|---|---|---|
| DE | 44 22 609 A1 | 1/1996 |
| EP | 0 674 002 A1 | 9/1995 |
| WO | 94/16064 A1 | 7/1994 |
| WO | 96/00772 A1 | 1/1996 |
| WO | 98/17768 A1 | 4/1998 |
| WO | 1998/13464 A1 | 4/1998 |
| WO | 2006053564 A1 | 5/2006 |
| WO | WO-2011027892 A1 * | 3/2011 ............. A01N 59/16 |

* cited by examiner

*Primary Examiner* — Vasudevan S Jagannathan
*Assistant Examiner* — Preeti Kumar
(74) *Attorney, Agent, or Firm* — Eric Fechter

(57) ABSTRACT

The storage stability of enzyme granules for detergents can be improved by incorporating a polyamine having a molecule with at least 10% w/w of nitrogen wherein at least 50% of the N atoms are present as amines.

19 Claims, No Drawings ns; polyvinylamines; poly(l-aminobuta-diene); amine-terminated hyperbranched polyurea; poly(aminoethyl methacrylate) and aminoethylated acrylic polymers; amine terminated poly(butadiene-co-acrylonitrile); polyamino-substituted mono-, di-, oligo-, poly-saccharides; dendrimers comprising one or more amine moieties; poly(amino acids); amino functionalized polydialkylsiloxane; polyaminoalkyls and mixtures thereof.

STORAGE-STABLE ENZYME GRANULES

CROSS-REFERENCE TO RELATED APPLICATIONS

This application is a 35 U.S.C. 371 national stage application of PCT/EP2012/063131 filed Jul. 5, 2012 which claims priority or the benefit under 35 U.S.C. 119 of European application no. 11173592.4 filed Jul. 12, 2011 and U.S. provisional application no. 61/506,839 filed Jul. 12, 2011, the contents of which are fully incorporated herein by reference.

FIELD OF THE INVENTION

The present invention relates to enzyme granules. More particularly, it relates to enzyme granules with enhanced storage stability during storage by themselves or during storage as part of a granular detergent.

BACKGROUND OF THE INVENTION

Enzymes in the form of granules are commonly used in granular (powder) detergents, and storage stability is a prime concern, both during storage of the enzyme granules per se and as ingredients in granular detergents.

The improvement of the storage stability of enzyme granules for detergents has received much attention in the prior art, and various additives have been proposed to improve the storage stability.

EP 0 674 002 A1, DE 44 22 609 A1, US 2010/078381 A1, WO 94/16064 A1, WO 98/17768 A1 and U.S. Pat. No. 6,872,297 A1 disclose various formulations of enzyme granules.

SUMMARY OF THE INVENTION

The inventors have found that the storage stability of enzyme granules by themselves or in a detergent can be improved by incorporating a polyamine.

Accordingly, the invention provides a granule having a core which comprises a homogeneous mixture comprising an enzyme in soluble form and a polyamine. The polyamine molecule contains at least 10% w/w of nitrogen, and at least 50% of the N atoms are present as amines. The invention further provides a method of preparing the granules and a granular detergent composition comprising the enzyme granules.

DETAILED DESCRIPTION OF THE INVENTION

Polyamine

The polyamine typically has three or more primary or secondary amino groups ($NH_2$ or NH). The polyamine molecule contains at least 10% w/w of nitrogen; it may contain at least 15% w/w of nitrogen, particularly at least 20%, at least 25% or at least 30%. At least 60% of the N atoms in the polyamine molecule may be present as amines (primary, secondary and tertiary), particularly at least 70%, at least 80% or at least 90%. At least 50% of the N atoms may be present as primary or secondary amines, particularly at least 55%, at least 60%, at least 65% or at least 70%.

One example of a useful polyamine is a cationic polymer based on ethylene imine, particularly polyethylene imine. Useful polyamines also include: polylysine; polyalkylamines; polyallylamines; polyvinylamines; poly(l-aminobuta- The polyamine may have an average molecular weight (weight average) above 800 Da, particularly above 1200 Da, above 1500 Da or above 2000 Da. The average molecular weight may be below 2,000,000 Da, particularly below 1,000,000 Da, below 100,000 Da, below 20,000 or below 10,000 Da. The polyamine may be present in an amount of 0.1-10%, or 0.2-5% by weight of the mixture (the uncoated core), particularly 0.5-2%.

Polyethyleneimine

Polyethyleneimine (PEI) is a cationic polymer which may be linear or branched. Linear PEI consists of a polymeric chain with —NH—$CH_2$—$CH_2$— as the repeating unit, and essentially all the N atoms are present as secondary amines. Branched PEI may be prepared by polymerization of ethylene imine, also known as azeridine. The ratio of secondary to primary amines in the branched PEI may be above 0.7, particularly above 0.9 or above 1.1; the ratio may be below 2, particularly below 1.5, below 1.25 or below 1. The ratio of tertiary to primary amines in the branched PEI may be above 0.4, particularly above 0.5, above 0.6, or above 0.7; the ratio may be below 1, particularly below 0.8 or below 0.6, Optional Salt of a Polyvalent Cation For improved storage stability, the mixture in the granule core may further comprise a salt of a polyvalent cation, particularly a divalent cation. At 25° C., the salt has a solubility in water above 0.01 g/100 mL, particularly above 0.1 g/100 mL, above 1 g/100 mL or above 10 g/100 mL.

The cation may be $Zn^{++}$, $Mg^{++}$, $Cu^{++}$ or $Mn^{++}$. The anion of the soluble salt may be organic or inorganic, e.g. sulfate, acetate, nitrate, phosphate, citrate, formate, chloride, or sulfite) The salt may be anhydrous or in the form of a hydrate. Particular examples are $MgSO_4.7H_2O$, $ZnSO_4.7H_2O$, and zinc acetate, Mg-acetate, $MgCl_2$, $ZnCl_2$, $Mg(NO_3)_2$, $Zn(NO_3)_2$, $ZnSO_3$, Mg-citrate, Zn-citrate.

The mixture may comprise the salt or combination of salts in an amount of 0.01-90% by weight, more particular 0.05-50% even more preferred 0.1-20%, or 0.1-10% (calculated in anhydrous form). The mixture typically comprises the cation (e.g. Zn and/or Mg) in an amount of 0.005-5% or more preferred 0.01-2%.

Enzyme

The enzyme may be a hydrolase (Enzyme Nomenclature EC 3), a lipase, a cutinase, a protease, an amylase, a cellulase, a mannanase, a lyase or a pectate lyase.

Lipase and Cutinase

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g. *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO2007/087508 and WO 2009/109500.

Preferred commercially available lipase enzymes include Lipolase™, Lipolase Ultra™, and Lipex™; Lecitase™, Lipolex™; Lipoclean™, Lipoprime™ (Novozymes NS). Other commercially available lipases includes Lumafast (Genencor Int Inc); Lipomax (Gist-Brocades/Genencor Int Inc) and *Bacillus* sp lipase from Solvay.

Protease

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™, Everlase™, Polarzyme™ (Novozymes NS), Maxatase™, Maxacal™, Maxapem™, Properase™, Purafect™, Purafect OxP™ FN2™ and FN3™ (Genencor International Inc.).

Amylase

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Stainzyme; Stainzyme Plus; Duramyl™, Termamyl™, Termamyl Ultra; Natalase, Fungamyl™ and BAN™ (Novozymes NS), Rapidase™ and Purastar™ (from Genencor International Inc.).

Lyase

The lyase may be a pectate lyase derived from *Bacillus*, particularly *B. lichemiformis* or *B. agaradhaerens*, or a variant derived of any of these, e.g. as described in U.S. Pat. No. 6,124,127, WO 1999/027083, WO 1999/027084, WO 2002/006442, WO 2002/092741, WO 2003/095638, A commercially available pectate lyase is XPect; Pectawash and Pectaway (Novozymes NS).

Mannanase

The mannanase may be an alkaline mannanase of Family 5 or 26. It may be a wild-type from *Bacillus* or *Humicola*, particularly *B. agaradhaerens, B. licheniformis, B. halodurans, B. clausii,* or *H. insolens*. Suitable mannanases are described in WO 1999/064619. A commercially available mannanase is Mannaway (Novozymes NS).

Cellulase

Suitable cellulases may be of bacterial or fungal origin. Chemically or genetically modified mutants are included. It may be a fungal cellulase from *Humicola insolens* (U.S. Pat. No. 4,435,307) or from *Trichoderma*, e.g. *T. reesei* or *T. viride*. Examples of cellulases are described in EP 0 495 257. Commercially available cellulases include Carezyme™, Celluzyme™, Celluclean™, Celluclast™, and Endolase™; Renozyme; Whitezyme (Novozymes NS) Puradax, Puradax HA, and Puradax EG (available from Genencor).

Enzyme Core

The homogeneous mixture comprising the enzyme and the polyamine (the enzyme core) contains the enzyme in a form that will dissolve upon dilution in water or wash liquor. The solubility may be determined, e.g., by the dissolution test described later in this specification.

The enzyme is substantially free of covalent links to the polyamine. Thus, the molecular weight of the enzyme present in the granules is not substantially different from the molecular weight of the enzyme polypeptide alone, e.g. the average molecular weight of the enzyme present in the granules is within +/−500 Da from the enzyme polypeptide. It is preferred that no amine cross-linking agents like e.g. glutaraldehyde or imidoester as known in the art is added to the composition to avoid immobilization of the enzyme by covalent reaction with e.g. the added polyamine and covalent reaction of the polyamine to insoluble particles of the formulation.

Methods for preparing the core can be found in Handbook of Powder Technology; Particle size enlargement by C. E. Capes; Volume 1; 1980; Elsevier. Preparation methods include known feed and granule formulation technologies, i.e.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in e.g. WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme. (Michael S. Showell (editor); *Powdered detergents*; Surfactant Science Series; 1998; vol. 71; page 140-142; Marcel Dekker)

e) Prilled products, wherein an enzyme-containing powder is suspended in molten wax and the suspension is sprayed, e.g. through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); *Principles of Powder Technology*; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. Other known methods for drying granules in the feed or enzyme industry can be used by the skilled person. The drying preferably takes place at a product temperature of from 25 to 90° C. For some enzymes it is important the cores comprising the enzyme contain a low amount of water before coating with the salt. If water sensitive enzymes are coated with a salt before excessive water is removed, it will be trapped within the core and it may affect the activity of the enzyme negatively. After drying, the cores preferably contain 0.1-10% w/w water.

Optional Coating
Salt Coating

The granule comprises a core which may be uncoated or may be surrounded by at least one coating. The coating may comprise at least 60% by weight w/w of a salt, e.g. at least 65%, at least 70%, at least 75%, at least 80%, at least 85%, at least 90%, at least 95% or at least 99% by weight w/w.

The coating may be applied in an amount of at least 5% by weight of the core, e.g. at least 10%, 10% or 15%. The amount may be at most 70%, 50%, 40% or 30%.

To provide acceptable protection, the salt coating is preferably at least 1 µm thick, particularly at least 2 µm, at least 4 µm or at least 8 µm. The thicker the coating the more time consuming and expensive it gets to produce the granule. In a particular embodiment the thickness of the salt coating is below 100 µm. In a more particular embodiment the thickness of the salt coating is below 60 µm. In an even more particular embodiment the total thickness of the salt coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness. The salt may be added from a salt solution where the salt is completely dissolved or from a salt suspension wherein the fine particles is less than 50 µm, such as less than 10 µm or less than 5 µm. It is preferred that the salt is present as a continuous phase in the coating layer The salt coating can further contain other materials as known in the art, e.g. fillers, antisticking agents, pigments, dyes, plasticizers and f/or binders, such as titanium dioxide, kaolin, calcium carbonate or talc.

It is preferred that the continuous part of the coating layer (as opposed to discrete filler particles) constitutes at least 50% w/w of the coating, more preferred more than 60%, 75%, 90%, or 95%.

Salts

The salt coating may comprise a single salt or a mixture of two or more salts. The salt may be water soluble, in particular having a solubility of at least 5 grams in 100 g of water at 20° C., preferably at least 10 g per 100 g water.

The salt may be an inorganic salt. Examples of cations in these salts are ammonium, sodium, potassium, and magnesium. Examples of anions include chloride, sulfate, phosphate, citrate. Specific examples include $NaH_2PO_4$, $Na_2HPO_4$, $Na_3PO_4$, $(NH_4)H_2PO_4$, $K_2HPO_4$, $KH_2PO_4$, $Na_2SO_4$, $K_2SO_4$, $KHSO_4$, $MgSO_4$, $Mg(NO_3)_2$, $(NH_4)_2SO_4$ and sodium citrate.

The salt may be in anhydrous form, or it may be a hydrated salt, i.e. a crystalline salt hydrate with bound water(s) of crystallization. Specific examples include anhydrous sodium sulfate ($Na_2SO_4$), anhydrous magnesium sulfate ($MgSO_4$), magnesium sulfate heptahydrate ($MgSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt it applied as a solution of the salt e.g. using a fluid bed.

Optional Additional Coating

The granule may optionally have one or more additional coatings, e.g. to further improve the storage stability or to reduce the dust formation. Example of suitable coating materials are polyethylene glycol (PEG), methyl hydroxypropyl cellulose (MHPC) and polyvinyl alcohol (PVA).

Test Method
Dissolution Test

The following dissolution test may be used to determine whether the enzyme in the core of the granule is in soluble form. The test serves to distinguish enzymes in soluble form from immobilized enzymes.

Water or a detergent solution (stirred for 30 min and filtered through a sheet of gauze) is adjusted to 20° C.±2° C. and placed under a 4-bladed propeller stirrer adjusted to 600 rpm±10 rpm. 75 mg of enzyme containing particle/l detergent solution is added at $T_0$. After addition of the enzyme containing particles the concentration of the enzyme released to the detergent solution is measured every 15 seconds for the first 60 seconds by withdrawing samples from the detergent solution and filtering. Subsequently samples are taken out every 30 seconds until 120 seconds and every 60 seconds until 1100 seconds. The time for 50% resp. 90% release of enzyme from the enzyme containing particles are calculated. The enzyme in the core is considered to be in soluble form if the time for 90% release is below 10 minutes, particularly below 5 minutes or below 3 minutes, or if the time for 50% release is below 5 minutes, particularly below 2.5 minutes or below 1.5 minutes.

The enzyme activity in the withdrawn samples may be measured by a suitable analytical method, e.g. for a lipase enzyme by use of assays involving synthetic substrates such as p-nitrophenyl butyrate or p-nitrophenyl palmitate. Alternatively, the enzyme release may be found by determining the amount of enzyme protein in the detergent solution or water instead of determining the enzyme activity.

Detergent Composition

The granules are particularly suited for incorporation in a granular detergent composition comprising a surfactant. Enzyme granules according to the invention result in improved storage stability of the enzyme when the granules are incorporated in a detergent, even a detergent comprising aggressive components such as a bleaching system.

The detergent composition may for example be formulated as a laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

The detergent composition of the invention may be in any convenient dry form, e.g., a bar, a tablet, a powder, a granulate or a paste. It may also be a liquid detergent, either an aqueous or non-aqueous liquid detergent.

Surfactant

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfosuccinic acid or soap, and combinations thereof.

Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

Non-limiting examples of zwitterionic surfactants include betaine, alkyldimethylbetaine, and sulfobetaine, and combinations thereof.

Builder or Complexing Agent

The detergent may contain 0-65% of a detergent builder or complexing agent such as zeolite, diphosphate, triphosphate, phosphonate, carbonate, citrate, nitrilotriacetic acid, ethylenediaminetraacetic acid, diethylenetriaminepentaacetic acid, alkyl- or alkenylsuccinic acid, soluble silicates or layered silicates (e.g. SKS-6 from Hoechst).

In a dish wash detergent, the level of builder is typically 40-65%, particularly 50-65%. The builder and/or co-builder may particularly be a chelating agent that forms water-soluble complexes with Ca and Mg. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may include include a co-builder alone, or in combination with a builder, for example a zeolite builder. Non-limiting examples of co-builders include homo-polymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenyl-succinic acid. Additional specific examples include 2,2',2"-nitrilotriacetic acid (NTA), etheylene-diaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene) tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl)glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(hydroxyethyl)-ethylidenediaminetriacetate (H EDTA), diethanolglycine (DEG), Diethylenetriamine Penta (Methylene Phosphonic acid) (DTPMP), amino-tris(methylenephosphonic acid) (ATMP), and combinations and salts thereof. Further exemplary builders and/or co-builders are described in, e.g., WO 09/102854, U.S. Pat. No. 5,977,053.

Polymer

The detergent may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

Bleaching System

The detergent may contain a bleaching system, which may comprise a $H_2O_2$ source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. Suitable photobleaches may for example be sulfonated zinc phthalocyanine. Suitable bleach activators include 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy)benzenesulfonate (NOBS), and/or those disclosed in WO98/17767. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

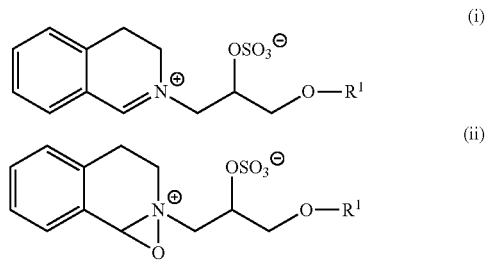

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs, as found for surfactants and lipids forming miceller, lamellar or other well defined meso-phases. Instead, many hydrotropes show a continuous-type aggregation process where the size of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Fabric Hueinq Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Detergent Formulations

The enzyme granules may be included in a granular detergent formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, WO09/015951, WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, or WO2010000636.

EXAMPLES

Example 1

A typical formulation is a high-shear T-granulate as produced e.g. in example 1 of WO03/000456 (containing enzyme, Na-sulfate, cellulose fibers and a binder, e.g. sucrose or dextrin) with the following formulation in the core (% by weight of uncoated dry granulate):

4% by weight Zinc sulfate heptahydrate

1% by weight of a 50% Polyamine solution (e.g. polyethylene-imine) These stabilizers are preferably added to the aqueous enzyme concentrate before granulation.

After granulation and drying a 40% by weight (% by weight of dry uncoated granulate) Na-sulfate coating is applied under relatively humid condition (around 50% by weight RH in the outgoing air) in a fluid bed (e.g. as produced in example 4 of WO03/000456). The Na-sulfate solution applied is kept over 32° C. during the coating. A cosmetic and dust reducing outer thin film is further applied in coating mixer (2.5% PEG4000:TiO$_2$ 1:1 w/w).

Example 2

A Lipase granulate is made with the following composition. The amounts are given in relation to the raw (uncoated) granulate. The granules are made by high shear granulation and coated by fluid bed coating followed by polymer coating in coating mixer. The polyamine was a branched modified polyethyleneimine (PEI, Lupasol PO 100, product of BASF). It has an average molecular weight of 5000, and is added in an amount of 1% w/w of a product with a PEI content of 50%.

| Ingredient | Typical range (% by weight of uncoated granule) |
|---|---|
| Core | |
| Cellulose fibers | 10% by weight |
| Carbohydrate binder (e.g. dextrin and/or sucrose) | 6% by weight |
| ZnSO$_4$•7H$_2$O | 4% by weight |
| Polyamine (50% solution) | 1% by weight (0.5% polyamine solids) |
| Lipase enzyme concentrate | 1-3% by weight (solids) |
| Na$_2$SO$_4$ | Add to 100% by weight About 70% by weight (excl. coating) |
| Coating | |
| Na$_2$SO$_4$ | 40% by weight |

Example 3

A number of enzyme granulates were prepared by mixing enzyme and stabilizers as shown in the table below and granulating in a mixer. A salt coating and film coating were applied as indicated. Each granular was then added to a granular bleach detergent or a granular non-bleach detergent and stored at 37° C., 70% relative humidity or 35° C., 55% relative humidity. Amounts are given as % by weight in relation to the weight of the core. The salt coating was applied in an amount of 40% by weight of the core. The polyamine was the same polyethyleneimine (given as the amount of 50% solution) as in Example 2.

| ID | Enzyme | Stabilizers in core | Coating | Residual activity after 4 weeks in bleach detergent at 35 C., 55% rh | Residual activity after 2 weeks in bleach detergent at 37 C., 70% rh | Residual activity after 2 weeks in non-bleach detergent at 37 C., 70% rh |
|---|---|---|---|---|---|---|
| A | Lipase Y | — | — | 39% | 1% | 21% |
| B | Lipase Y | 4% Zn-sulfate 7H$_2$O | — | 41% | 4% | 54% |
| B1 | Lipase Y | 4% Zn-sulfate 7H$_2$O 0.5% Polyamine | — | 53% | 5% | 57% |
| B2 | Lipase Y | 4% Zn-sulfate 7H$_2$O 1% Polyamine | — | 58% | 5% | 65% |
| B3 | Lipase Y | 4% Zn-sulfate 7H$_2$O 2% Polyamine | — | 66% | 5% | 68% |
| C | Lipase X | 4% Zn-sulfate 7H$_2$O 1% Polyamine | — | 64% | 17% | 74% |
| D | Lipase X | 4% Zn-sulfate 7H$_2$O 1% Polyamine | 40% Na-sulfate | 81% | 45% | 100% |
| E | Lipase Y | 4% Mg-sulfate 7H$_2$O 2% Polyamine | — | 62% | 9% | 50% |
| F | Lipase Y | 4% Mg-sulfate 7H$_2$O 1% Polyamine | 40% Na-sulfate | 70% | 17% | 53% |

The results demonstrate the effect of adding a polyamine, a multivalent cation and applying a salt coating. Thus, a comparison of the results for granulates A and B shows the effect of adding a multivalent cation; a comparison of the results for granulates B and C shows the effect of adding a polyamine; a comparison of the results for granulates C and D (or E and F) shows the effect of applying a salt coating; a comparison of the results for granulates C and E shows that the generic stabilizing effect with an alternative cation.

Example 4

Two enzyme granulates were prepared by mixing enzyme and stabilizers as shown in the table below and granulating in a mixer. Each granulate was then added to a granular bleach detergent or a granular non-bleach detergent and stored at 37° C., 70% relative humidity or 35° C., 55% relative humidity. Amount of stabilizer is given as % by weight in relation to the weight of the core. The polyamine was the same polyethyleneimine as in Example 2.

| ID | Enzyme | Stabilizers in core | Coating | Residual activity after 2 weeks in bleach detergent at 35 C., 55% rh | Residual activity after 1 week in non-bleach detergent at 37 C., 70% rh |
|---|---|---|---|---|---|
| G | Lipase Y | — | — | 71% | 53% |
| H | Lipase Y | 2% Polyamine | — | 81% | 72% |

The results demonstrate the stabilizing effect of adding a polyamine. Thus, a comparison of the results for granulates G and H shows the effect of adding a polyamine. The results in Example 3 and Example 4 demonstrate that the stabilizing effect of adding a polyamine is a generic effect as it stabilizes different enzymes.

Example 5

A Cellulase granulate is made with the following composition. The amounts are given in relation to the raw (uncoated) granulate. The granules are made by high shear granulation and coated by fluid bed coating or by polymer coating in coating mixer.

| Ingredient | Typical range (% by weight of uncoated granule) |
|---|---|
| Core | |
| Cellulose fibers | 10% by weight |
| Carbohydrate binder (e.g. dextrin and/or sucrose) | 9% by weight |
| MgSO$_4$•7H$_2$O | 5% by weight |
| Polyamine solids | 0.5% by weight |
| Cellulase enzyme concentrate | 2-4% by weight (solids) |
| CaCO$_3$ | 8% |

| Ingredient | Typical range (% by weight of uncoated granule) |
|---|---|
| Na$_2$SO$_4$ | Add to 100% by weight About 70% by weight (excl. coating) |
| Coating | |
| Na$_2$SO$_4$ | 40% by weight |

The polyamine used was Lupasol G100 (with a polyethyleneimine content of 50% w/w added in an amount of 1% w/w). It is a branched homopolymeric polyethyleneimine with M$_w$≈5000. The ratio of prim:sec:tert amines is approx. 1:1.05:0.76.

Example 6

A number of enzyme granulates were prepared by mixing enzyme and stabilizers as shown in the table below and granulating in a mixer. A salt coating and film coating were applied as indicated. Each granulate was then added to a granular bleach detergent or a granulate non-bleach detergent and stored at 37° C., 70% relative humidity. Amounts are given as % by weight in relation to the weight of the core. The salt coating was applied in an amount of 40% by weight of the core. The PEG (polyethylene glycol) wax coating was prepared in a mixer.

| ID | Enzyme type | Amount and brand of Polyamine | Type of Polyamine | Other core stabilizers | Coating |
|---|---|---|---|---|---|
| A | Lipase | 1% Lupasol PN50 (50% w/w) | Branched polyethyleneimine (M$_w$ ≈ 1000000) | 5% Mg-sulfate 7H$_2$O | 40% Na-sulfate |
| B | Lipase | 1% Epomin P-1050 (50% w/w) | Branched polyethyleneimine (M$_w$ ≈ 70000) | 5% Mg-sulfate 7H$_2$O | 40% Na-sulfate |
| C | Lipase | 0.5% Aldrich 408719 | Branched polyethyleneimine (M$_w$ ≈ 800), | 5% Mg-sulfate 7H$_2$O | 40% Na-sulfate |
| D | Lipase | 1.0% Aldrich 482595 (50% w/w solution) Aldrich 482595 | Branched polyethyleneimine (M$_w$ ≈ 1200), | 5% Mg-sulfate 7H$_2$O | 40% Na-sulfate |
| E | Lipase | 1% Lupasol G100 (50% w/w) | Branched polyethyleneimine (M$_w$ ≈ 5000) | 5% Mg-sulfate 7H$_2$O | 40% Na-sulfate |
| F | Cellulase | 1% Lupasol PN50 (50% w/w) | Branched polyethyleneimine (M$_w$ ≈ 1000000) | 5% Mg-sulfate 7H$_2$O, 2% Na-citrate, 0.7% citric acid | 40% Na-sulfate |
| G | Cellulase | 1% Epomin P-1050 (50% w/w) | Branched polyethyleneimine (M$_w$ ≈ 70000) | 5% Mg-sulfate 7H$_2$O, 2% Na-citrate, 0.7% citric acid | 40% Na-sulfate |
| H | Cellulase | 0.5% Aldrich 408719 | Branched polyethyleneimine (M$_w$ ≈ 800), | 5% Mg sulfate 7H$_2$O, 2% Na-citrate, 0.7% citric acid | 40% Na-sulfate |

| ID | Enzyme | Stabilizers in core | Coating | Residual activity after 1 week in bleach detergent at 37 C., 70% rh | Residual activity after 2 weeks in bleach detergent at 37 C., 70% rh | Residual activity after 4 weeks in non-bleach detergent at 37 C., 70% rh | Residual activity after 6 weeks in non-bleach detergent at 37 C., 70% rh |
|---|---|---|---|---|---|---|---|
| A | Cellulase | — | 8% PEG4000 + 7% CaCO3 + 7% TiO$_2$ | 34% | 0% | 6% | 4% |
| B | Cellulase | 5% Mg-sulfate 7H$_2$O | 40% Na-sulfate | 89% | 43% | 50% | 29% |
| C | Cellulase | 5% Mg-sulfate 7H$_2$O 1% Lupasol G100 | 40% Na-sulfate | 82% | 58% | 61% | 57% |
| D | Cellulase | 5% Mg-sulfate 7H$_2$O 1% Lupasol G100 2% Na-citrate 0.7% citric acid | 40% Na-sulfate | 87% | 72% | 83% | 81% |

The results demonstrate the effect of adding a polyamine, a multivalent cation, a citrate buffer and applying a salt coating. Thus, a comparison of the results for granulates A and B shows the effect of adding a multivalent cation and applying a coating; a comparison of the results for granulates B and C shows the effect of further adding a polyamine; a comparison of the results for granulates C and D shows the effect of applying a citrate buffer.

Example 7

Enzyme granulates varying polyamines as additive in the core has been prepared and added to powder detergents:

| ID | Enzyme type | Amount and brand of Polyamine | Type of Polyamine | Other core stabilizers | Coating |
|---|---|---|---|---|---|
| I | Cellulase | 1.0% (50% w/w solution) Aldrich 482595 | Branched polyethyleneimine (M$_w$ ≈ 1200), | 5% Mg-sulfate 7H$_2$O, 2% Na-citrate, 0.7% citric acid | 40% Na-sulfate |
| J | Cellulase | 1% Lupasol G100 (50% w/w) | Branched polyethyleneimine (M$_w$ ≈ 5000) | 5% Mg-sulfate 7H$_2$O, 2% Na-citrate, 0.7% citric acid | 40% Na-sulfate |

The Lupasol products are available from BASF, Germany. Epomin P-1050 is a product of Nippon Shokubai, Japan. The Aldrich products are available from Sigma-Aldrich Co., LLC.

The invention claimed is:

1. A granule having a core, which core comprises a homogeneous mixture comprising an enzyme in soluble form and a polyamine having a molecule with at least 10% w/w of nitrogen wherein at least 50% of the N atoms are present as amines, wherein the enzyme is free of covalent links to the polyamine.

2. The granule of claim 1 wherein the polyamine is polyethyleneimine.

3. The granule of claim 1 wherein the polyamine has an average molecular weight above 800 Da and below 2,000,000 Da.

4. The granule of claim 1 wherein the polyamine is present in an amount of 0.1-10% by weight of the mixture in the core.

5. The granule of claim 1 wherein the mixture in the core further comprises a soluble salt of a polyvalent cation.

6. The granule of claim 5 wherein the cation is Zn, Mg, Cu or Mn.

7. The granule of claim 5 wherein the soluble salt is a sulfate or acetate.

8. The granule of claim 5 wherein the soluble salt is present in an amount of 0.1-20% by weight in anhydrous form.

9. The granule of claim 1 wherein the core comprises zinc acetate in an amount of 1-5% by weight of the core.

10. The granule of claim 1 wherein the enzyme is a lipase, a cutinase, an amylase, a carbohydrase, a cellulase, a pectinase, a pectate lyase, a mannanase, an arabinase, a galactanase, a xylanase, an oxidase, a laccase, or a peroxidase.

11. The granule of claim 1 wherein the core has a coating comprising a salt.

12. A method of preparing a granule of claim 1, which comprises granulating with an aqueous solution comprising the enzyme and the polyamine.

13. A granular detergent composition comprising a surfactant and an enzyme granule of claim 1.

14. The granule of claim 4, wherein the polyamine is present in an amount of 0.2-5 by weight of the mixture in the core.

15. The granule of claim 4, wherein the polyamine is present in an amount of 0.5-2% by weight of the mixture in the core.

16. The granule of claim 5, wherein the mixture in the core further comprises a soluble salt of a divalent cation.

17. The granule of claim 8, wherein the soluble salt is present in an amount of 0.5-10% by weight in anhydrous form.

18. The granule of claim 8, wherein the soluble salt is present in an amount of 1-5 by weight in anhydrous form.

19. The granule of claim 11, wherein the coating is 5-70% by weight relative to the uncoated granule, wherein the coating comprises at least 60% by weight w/w of the salt and wherein the coating comprises a salt having a constant humidity at 20° C. of at least 60%.

* * * * *